(12) United States Patent
Ferree

(10) Patent No.: US 7,025,769 B1
(45) Date of Patent: Apr. 11, 2006

(54) SURGICAL FIXATION SYSTEM AND RELATED METHODS

(75) Inventor: Bret A. Ferree, Cincinnati, OH (US)

(73) Assignee: NuVasive, Inc., San Diego, CA (US)

( * ) Notice: Subject to any disclaimer, the term of this patent is extended or adjusted under 35 U.S.C. 154(b) by 287 days.

(21) Appl. No.: 10/455,113

(22) Filed: Jun. 4, 2003

Related U.S. Application Data

(60) Provisional application No. 60/384,966, filed on Jun. 4, 2002.

(51) Int. Cl.
*A61B 17/58* (2006.01)
(52) U.S. Cl. ...................................................... 606/69
(58) Field of Classification Search .................. 606/61, 606/69–71
See application file for complete search history.

(56) References Cited

U.S. PATENT DOCUMENTS

| | | | | |
|---|---|---|---|---|
| 6,306,139 B1 * | 10/2001 | Fuentes | ........................ | 606/70 |
| 6,458,133 B1 * | 10/2002 | Lin | .............................. | 606/69 |
| 6,599,290 B1 * | 7/2003 | Bailey et al. | .................. | 606/69 |
| 6,652,525 B1 * | 11/2003 | Assaker et al. | ............... | 606/61 |
| 6,669,700 B1 * | 12/2003 | Farris et al. | ................... | 606/69 |
| 6,695,846 B1 * | 2/2004 | Richelsoph et al. | .......... | 606/71 |

* cited by examiner

*Primary Examiner*—Eduardo C. Robert
*Assistant Examiner*—Michael J. Araj
(74) *Attorney, Agent, or Firm*—Jonathan Spangler

(57) ABSTRACT

A surgical fixation system including a surgical fixation plate, a plurality of fasteners, and a retainer having an improved mechanism to prevent the back out of screws employed in securing a surgical fixation plate to an intended orthopedic location.

30 Claims, 10 Drawing Sheets

SURGICAL FIXATION SYSTEM AND RELATED METHODS

CROSS-REFERENCE TO RELATED APPLICATION

This application claims the benefit of the filing date under 35 USC 119(e) of United States Provisional Application entitled "Anterior Cervical Plate," Ser. No. 60/384,966 filed Jun. 4, 2002, the entire contents of which is fully incorporated herein by reference.

BACKGROUND OF THE INVENTION

I. Field of the Invention

The present invention relates generally to the area of surgical fixation, and more particularly to a surgical fixation system having an improved mechanism to prevent the back out of screws employed in securing a surgical fixation plate to an intended orthopedic location.

II. Discussion of the Prior Art

The use of surgical fixation systems involving plates is accepted practice for a variety of orthopedic procedures. One procedure experiencing proliferated growth is that of spinal fusion, wherein a surgical fixation plate is secured along two or more vertebral bodies through the use of screws extending through bores formed in the plate. Secured in this fashion, the surgical fixation plates serve to immobilize the vertebral bodies. When employed with bone allograft or another fusion-effecting implant (such as a mesh cage, a threaded cage, etc. . . . ), this immobilization promotes fusion to occur between the adjacent vertebral bodies, which is intended to restore disk height between the vertebral bodies and reduce pain in the patient.

A challenge exists in the use of spinal fixation plates, however, in that the screws employed to fix the spinal fixation plate to the vertebral bodies have a tendency to back out from the plate over time. One application where this is particularly worrisome is with the use of a spinal fixation plate positioned over the anterior cervical spine. More specifically, such backing out may cause the screws to come into unwanted contact with the esophagus, which may lead to damage or impairment to that organ. Another problem is that, with the screws backed out (partially or fully), the mechanical properties of the overall construct will become compromised, which may lead to a loss in the height of the intervertebral space height and thereby cause pain to the patient.

Various efforts have been undertaken to prevent the back out of screws employed in prior art surgical fixation plates. Some include a plurality of elements or components to engage the head of the screw within the through bore. Others provide one or more elements or components to cover the through bore after the screw has been introduced into the intended orthopedic location (e.g. a vertebral body). Unfortunately, both types of prior art systems have various drawbacks or imperfections. The first type (with a plurality of parts to engage the head of the screw within the through bore) can be challenging due to the plurality of parts and associated instrumentation, which may disadvantageously increase surgical time. The second type (covering the head of the screw) can similarly be time consuming and challenging based on the need for additional instrumentation to place the cover. Both types of systems may be more costly based on the need for additional instrumentation above and beyond the screwdriver instrument.

The present invention is directed at overcoming, or at least reducing the effects of, one or more of the problems set forth above.

SUMMARY OF THE INVENTION

According to one broad aspect of the present invention, the present invention accomplishes this goal by providing a surgical fixation system including a plate, at least one fastener, and a retainer. The plate has at least one fastener-receiving aperture and at least one retainer-receiving aperture. The fastener-receiving aperture extends between an upper surface and a lower surface of the plate. The retainer-receiving aperture has a periphery defined by a plurality of tab members extending from the upper surface. The fastener has an anchor region and a head region. The anchor region is dimensioned to be passed through the fastener-receiving aperture for introduction into a surgical target site, and the head region is dimensioned to be received at least partially within the fastener-receiving aperture. The retainer is dimensioned to be introduced into the retainer-receiving aperture to overlap at least a portion of the head region of the fastener and thereby prevent the fastener from backing out of the fastener-receiving aperture.

According to another broad aspect of the present invention, the present invention accomplishes this goal by providing a method of surgical fixation is provided including the steps of: (a) positioning a plate over an intended surgical target site, the plate having at least one fastener-receiving aperture and at least one retainer-receiving aperture, the fastener-receiving aperture extending between an upper surface and a lower surface of the plate, and the retainer-receiving aperture having a periphery defined by a plurality of tab members extending from the upper surface; (b) introducing a fastener into the fastener-receiving aperture such that an anchor region of said fastener is introduced into the surgical target site and a head region of the fastener is received at least partially within the fastener-receiving aperture; and (c) introducing a retainer into the retainer-receiving aperture to overlap at least a portion of the head region of the fastener and thereby prevent the fastener from backing out of the fastener-receiving aperture.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical fixation plate disclosed herein boasts a variety of inventive features and components that warrant patent protection, both individually and in combination.

This invention improves upon the prior art by providing a surgical fixation system including a surgical fixation plate, a plurality of fasteners, and a retainer, wherein the retainer is configured and dimensioned to be received within a retainer-receiving aperture formed in the surgical fixation plate to prevent the fasteners from backing out over time. As will be described below, the retainer is capable of being easily introduced into the retainer-receiving aperture after the fasteners have been anchored into a given orthopedic target, which advantageously overcomes the drawbacks of the prior art. More specifically, back out prevention is accomplished in an easy to use and cost effective manner, in that simple off-the-shelf instrumentation may be used to deploy the retainer. Moreover, although particularly suited for use in anterior cervical spine fixation, it will be readily appreciated by those skilled in the art that the surgical fixation system of the present invention may be employed in any number of suitable orthopedic fixation procedures, including but not limited to lumbar spine fixation, thoracic spine fixation, as well as any non-spine fixation application such as bone fracture treatment.

Figure 1:
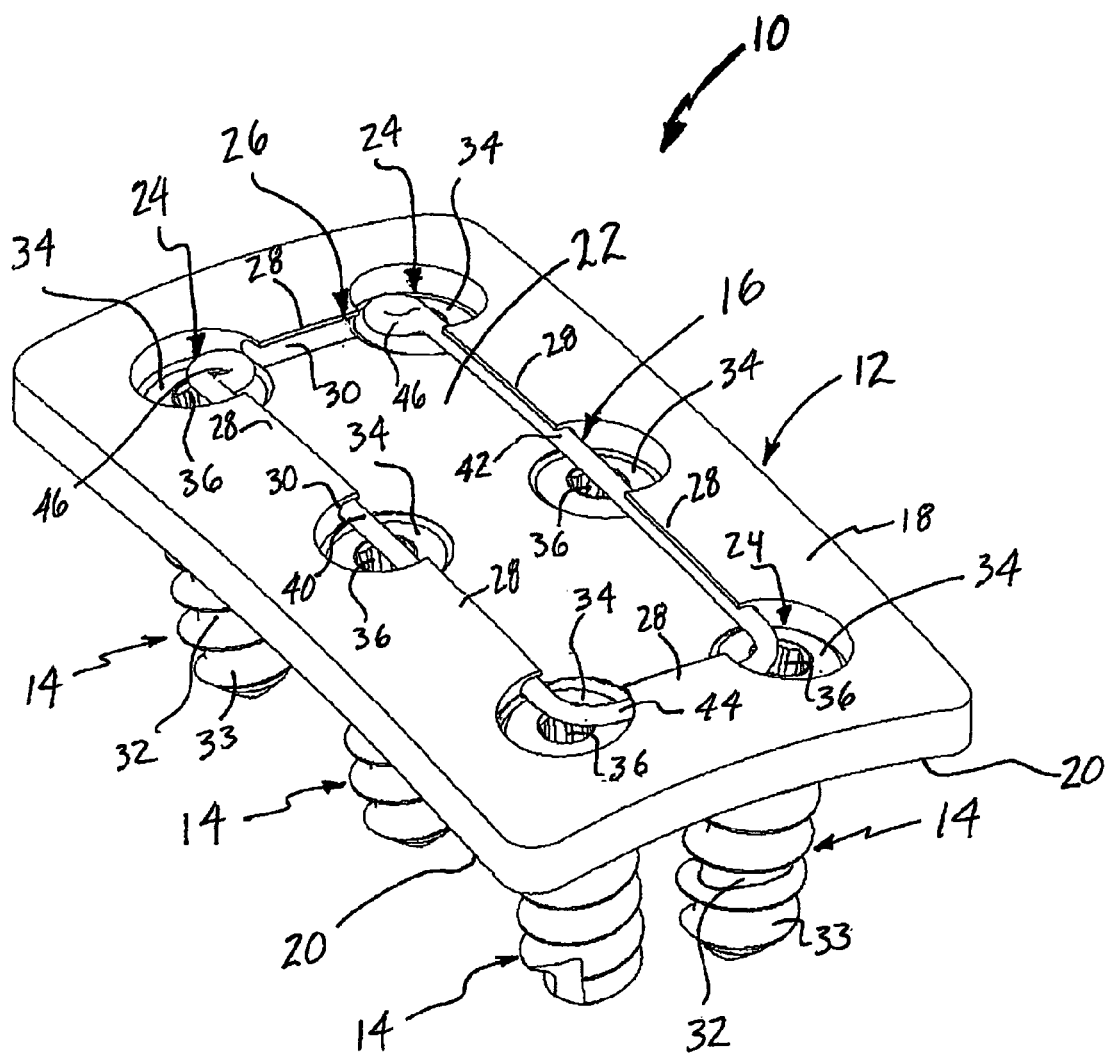
FIG. 1 is a perspective view of a surgical fixation system according to a one aspect of the present invention.
Figure 2:
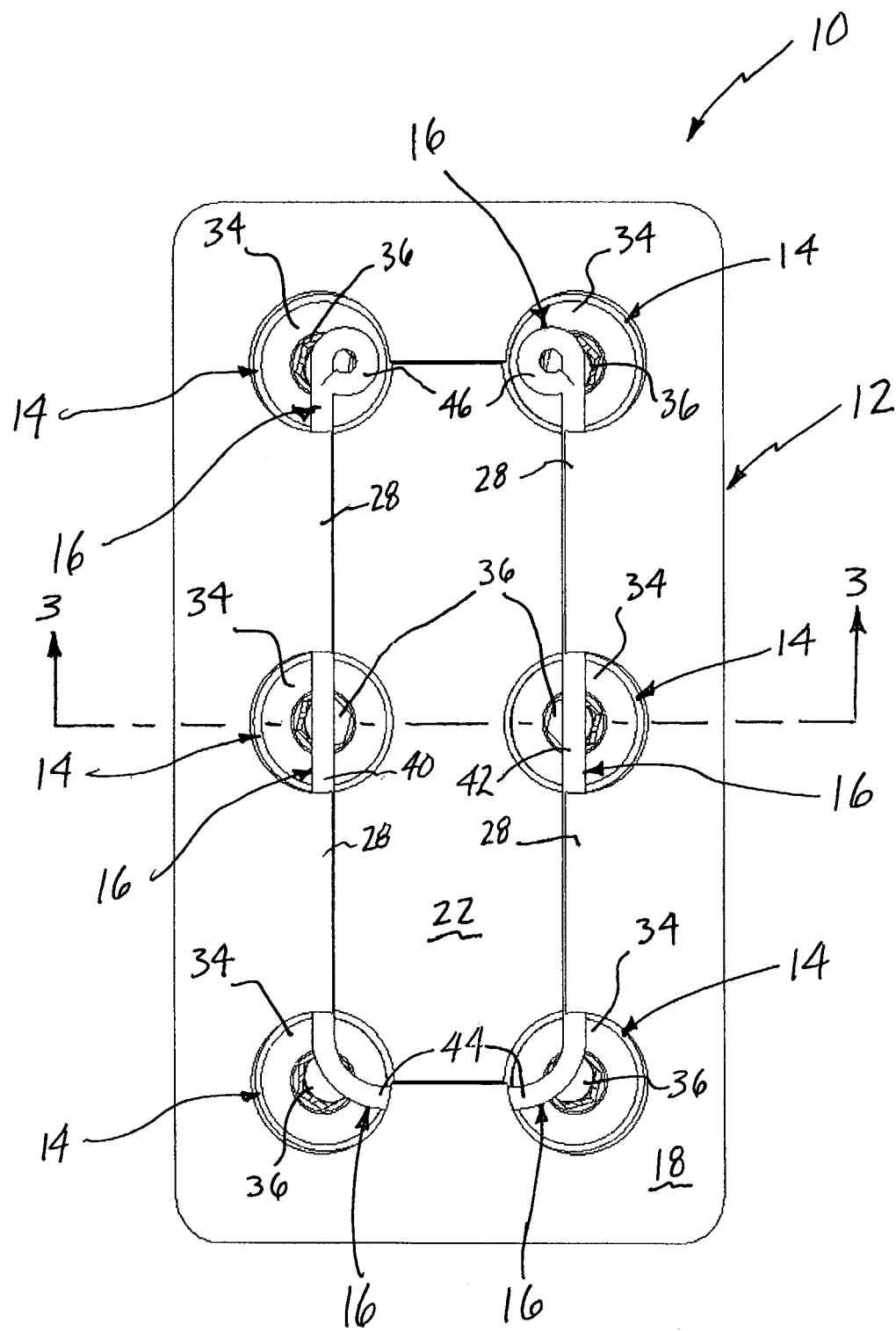
FIG. 2 is a top view of the surgical fixation system shown in FIG. 1.
Figure 3:
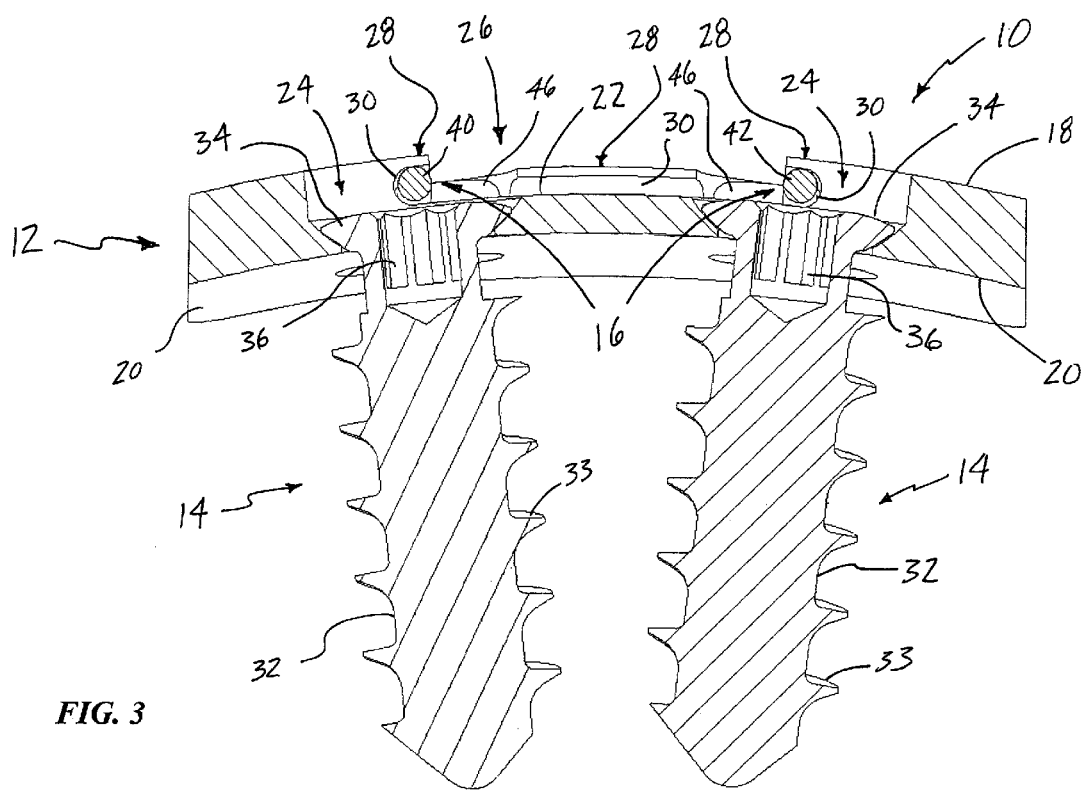
FIG. 3 is a cross-sectional view of the surgical fixation system taken along lines 3—3 in FIG. 2.

FIGS. 1–3 illustrate a surgical fixation system 10 according to a first broad aspect of the present invention. The surgical fixation system 10 comprises a surgical fixation plate 12, a plurality of fasteners 14, and a retainer 16. The surgical fixation plate 12 includes an upper surface 18, a lower surface 20, and an intermediate surface 22. A plurality of fastener-receiving apertures 24 is provided extending between the upper and lower surfaces 18, 20. A retainer-receiving aperture 26 is provided having a periphery defined by a plurality of tab members 28 extending from said upper surface 18. A groove 30 is defined between each tab member 28 and a region of the intermediate surface 22 extending generally beneath the tab member 28. In use as an anterior cervical plating system, the upper surface 18 would be the anterior-most (facing the esophagus of the patient) and the lower surface 20 would be the posterior-most (in general abutment with the anterior portion of the cervical spine). As best shown in FIG. 3, the plate 12 preferably has a curvature along both the upper and lower surfaces 18, 20. In this fashion, the upper surface 18 has a generally reduced cross-sectional profile to avoid impinging upon or inadvertently contacting the esophagus of the patient, and the lower surface 20 can best accommodate the general curvature of the spine. Although shown having a generally rectangular outer periphery (FIG. 2), the plate 12 may be provided having any number of suitable outer peripheral shapes, including but not limited to areas of reduced width between the fastener-receiving apertures 24. The plate 12 may be provided in any number of suitable fashions and dimensions depending upon the particular surgical procedure. For cervical spine fixation, the plate 12 may be (by way of example only) 2 mm thick between the upper surface 18 and lower surface 20, wherein the tab member 28 is preferably 0.2 mm thick, the groove 30 is preferably 0.9 mm thick, and the thickness between the intermediate surface 22 and the lower surface 20 is approximately 0.9 mm.

Each fastener 14 includes a shaft 32 and a head 34. The shaft 32 is dimensioned and configured to be passed through a fastener-receiving aperture 24 and anchored (such as via threads 33) into a boney target (such as a vertebral body in the cervical spine). The head 34 is dimensioned and configured to be received within the fastener-receiving aperture 24. In the embodiment shown, the concave curvature of the lower surface 20 causes the shaft 32 of the fasteners 14 to angle medially, generally towards one another. The head 34 of the fastener 14 may be equipped with any number of suitable mechanisms for engaging with a driving instrument, including but not limited to the hex-type female engagement portion 36. Although shown with six fasteners 14, it will be appreciated that the number of fasteners 14 (along with the number of fastener-receiving apertures 24) may be increased or decreased without departing from the scope of the invention. The fasteners 14 may be constructed from any number of biocompatible materials, and provided in any number of dimensions (including length, diameter, thread pitch), such that they are suitable for use as a bone screw.

The retainer 16 is dimensioned and configured to be introduced into the retainer-receiving aperture 26 and overlap at least a portion of the head 34 of each fastener 14 such that the retainer 16 prevents unwanted back out of fasteners 14 from the plate 12. In the embodiment shown, this is accomplished by providing the retainer 16 as a generally U-shaped member including a first elongate region 40, a second elongate region 42 disposed generally parallel to said first region 40, and a third elongate region 44 extending generally perpendicularly between the first and second regions 40, 42. The first and second regions 40, 42 are temporarily deformable relative to the third region 44 such that they may be forced towards one by applying force medially along a portion of the first and second regions 40, 42. This may be accomplished in any number of suitable fashions, including but not limited to engaging a tool (such as a pliers-type instrument) within loops 46 provided at the free ends of the first and second regions 40, 42 and clamping together. The third region 44 should be engaged at least partially under the tab member 28 at one end of the plate 12 such that the first and second regions 40, 42 while in a contracted state (not shown) may be rotated about the third region 44, introduced through the retainer-receiving aperture 26, and thereafter released such that portions of the first and second regions 40, 42 are disposed at least partially under the respective tab members 28. In this fashion, each fastener head 34 is covered by at least a portion of the retainer 16 to thereby prevent unwanted back out of fasteners 14 over time.

Figure 4:
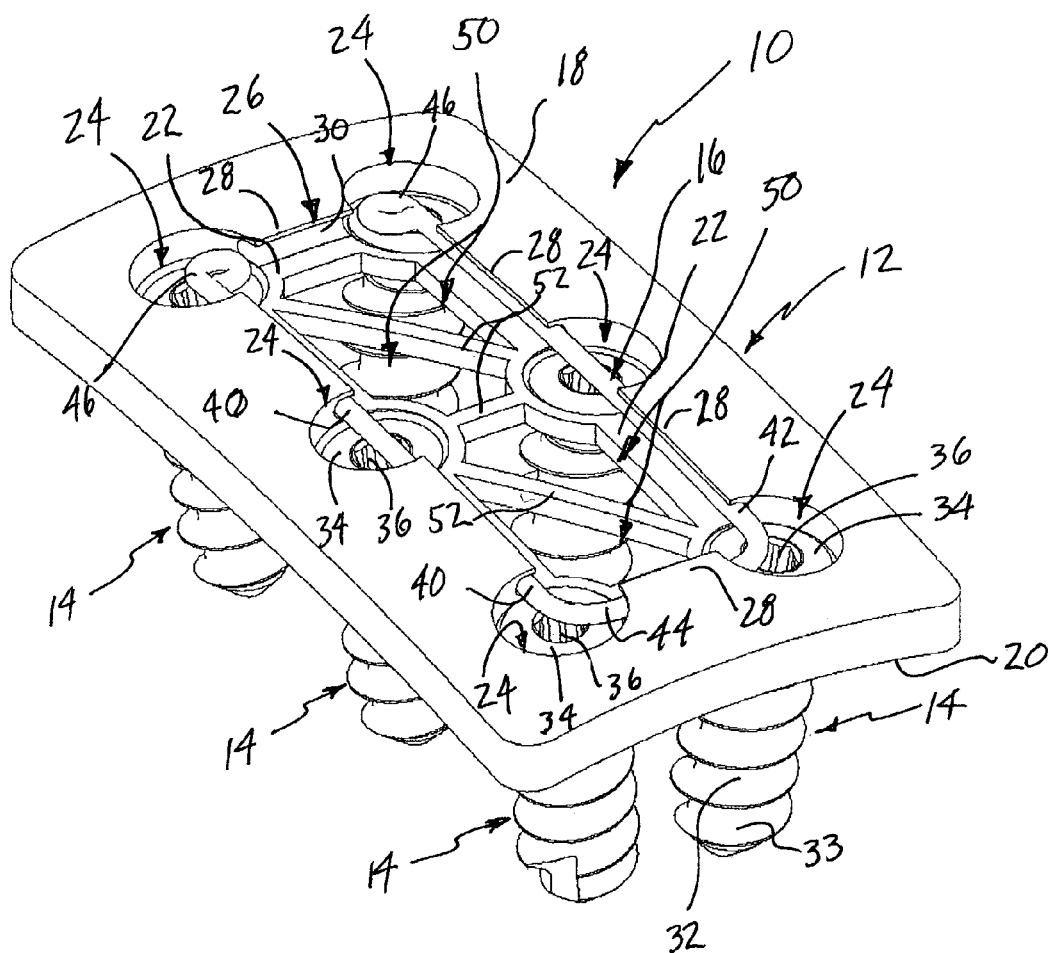
FIG. 4 is a perspective view of a surgical fixation system according to another broad aspect of the present invention.
Figure 5:
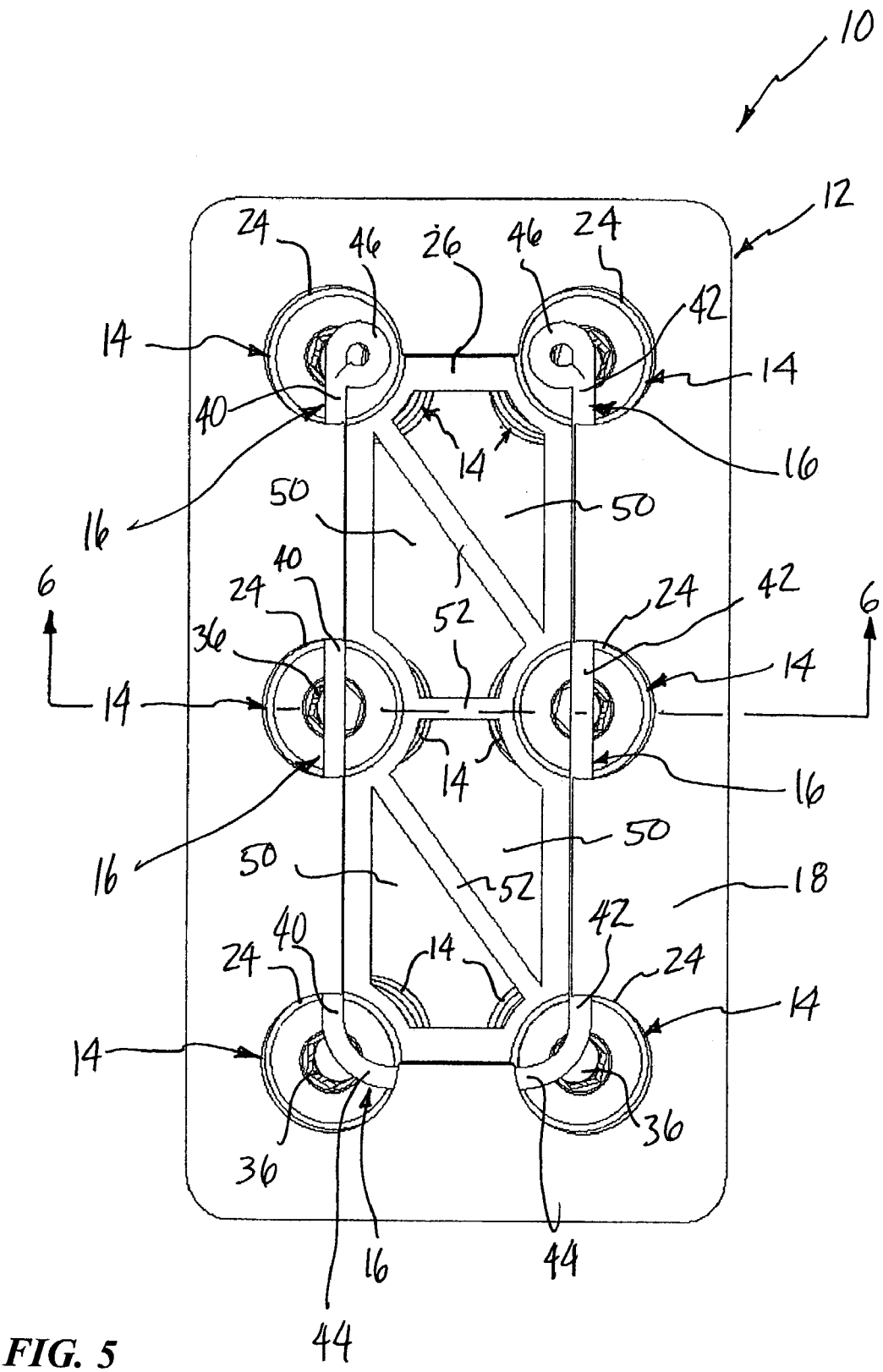
FIG. 5 is a top view of the surgical fixation system shown in FIG. 4.

The surgical fixation system 10 may be provided having a variety of additional features and/or various modifications without departing from the scope of the invention. For example, as shown in FIGS. 4–5, the surgical fixation system 10 may be equipped with one or more viewing apertures 50. This may be accomplished by removing portions of the plate 12 between the intermediate surface 22 and lower surface 20, which may (by way of example only) result in one or more struts or cross bars 52 extending side to side (angularly or straight) across the plate 12. In this fashion, the surgeon may visually inspect the surgical target site underneath portions of the plate 12 after placement on the spine. The viewing apertures 50 may be provided in any number of suitable geometries, including but not limited to the generally triangular shapes shown best in FIG. 5.

Figure 6:
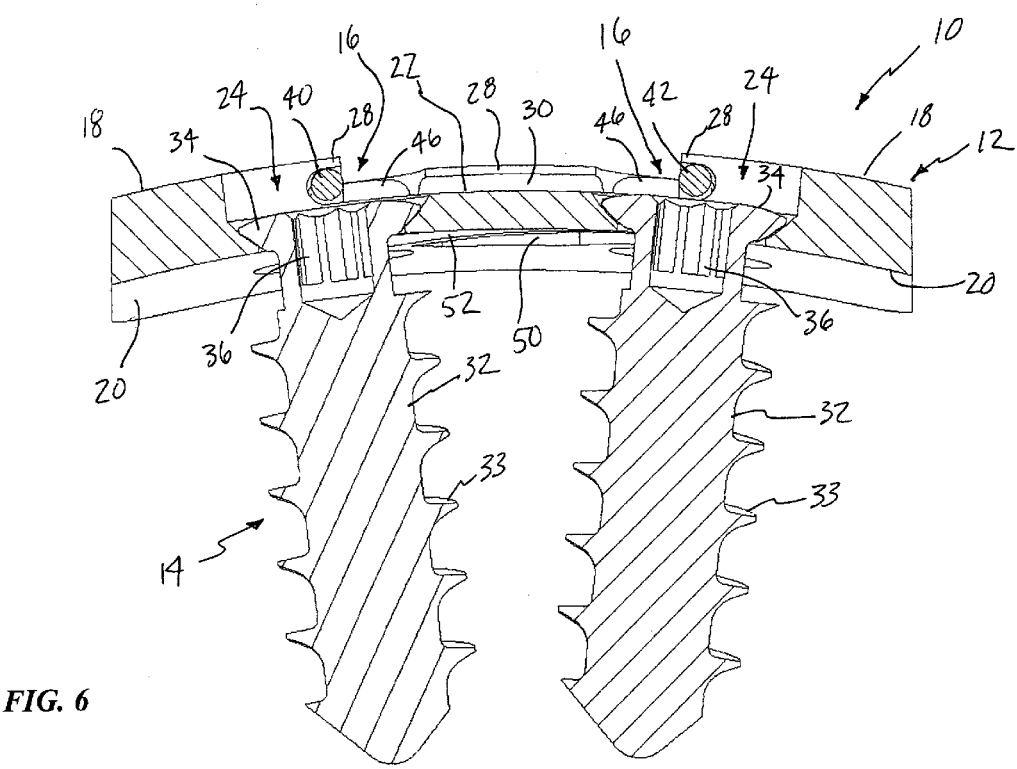
FIG. 6 is a cross-sectional view of the surgical fixation system taken along lines 6—6 in FIG. 5.
Figure 7:
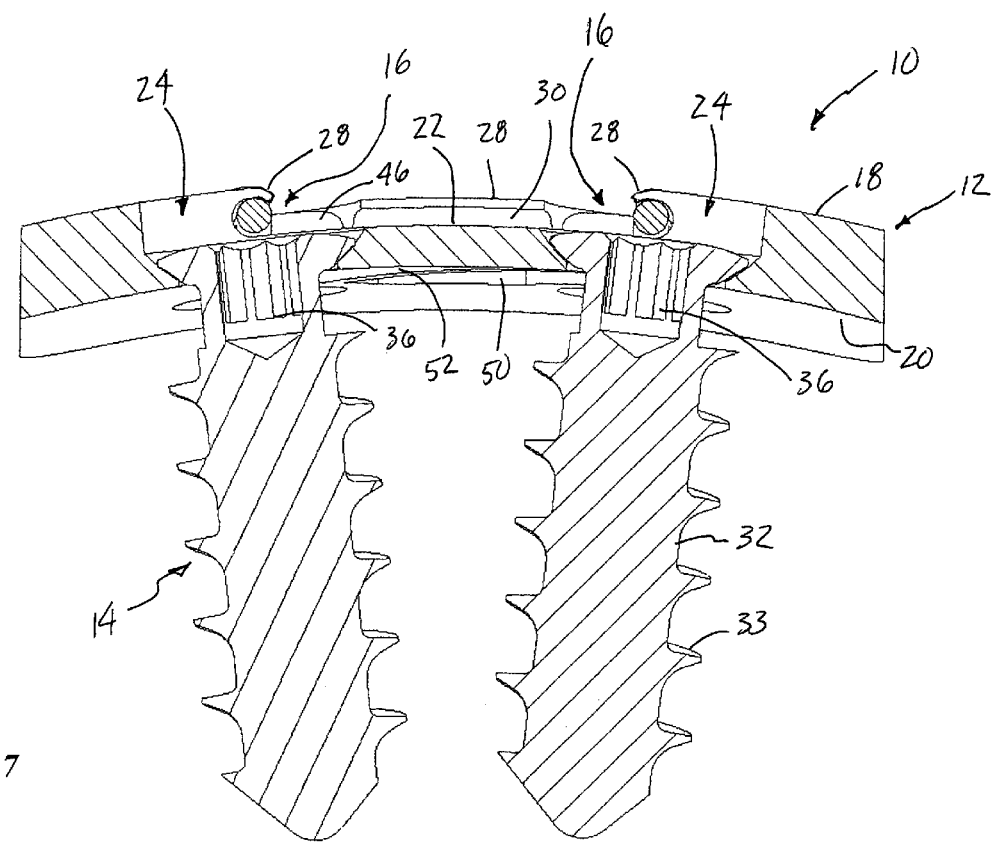
FIG. 7 is a cross-sectional view of the surgical fixation system shown in FIG. 6 with the tab member closed over at least a portion of the retainer according to a still further aspect of the present invention.

The tab members 28 may also be modified in any number of different fashions without departing from the scope of the present invention. For example, as shown in FIGS. 6–7, the tab members 28 may be deformed or otherwise moved such that the tab member 28 are brought to enclose a point or portions along the retainer 16 in an effort to prevent the retainer 16 from becoming dislodge or otherwise dissociated from the plate 12. More specifically, the tab members 28 may be moved from a first position shown in FIG. 6 (extending generally medially from the upper surface 18) into a second position shown in FIG. 7 (extending generally downward toward the intermediate surface 22 to enclose some or all of the retainer 16 depending upon the width of the tab member 28). In one embodiment, this manner of engagement (as well as others) may be employed to provide a hinged coupling arrangement between the third region 44 of the retainer 16 and the respective tab member 28 at one end of the plate 12.

Figure 8:
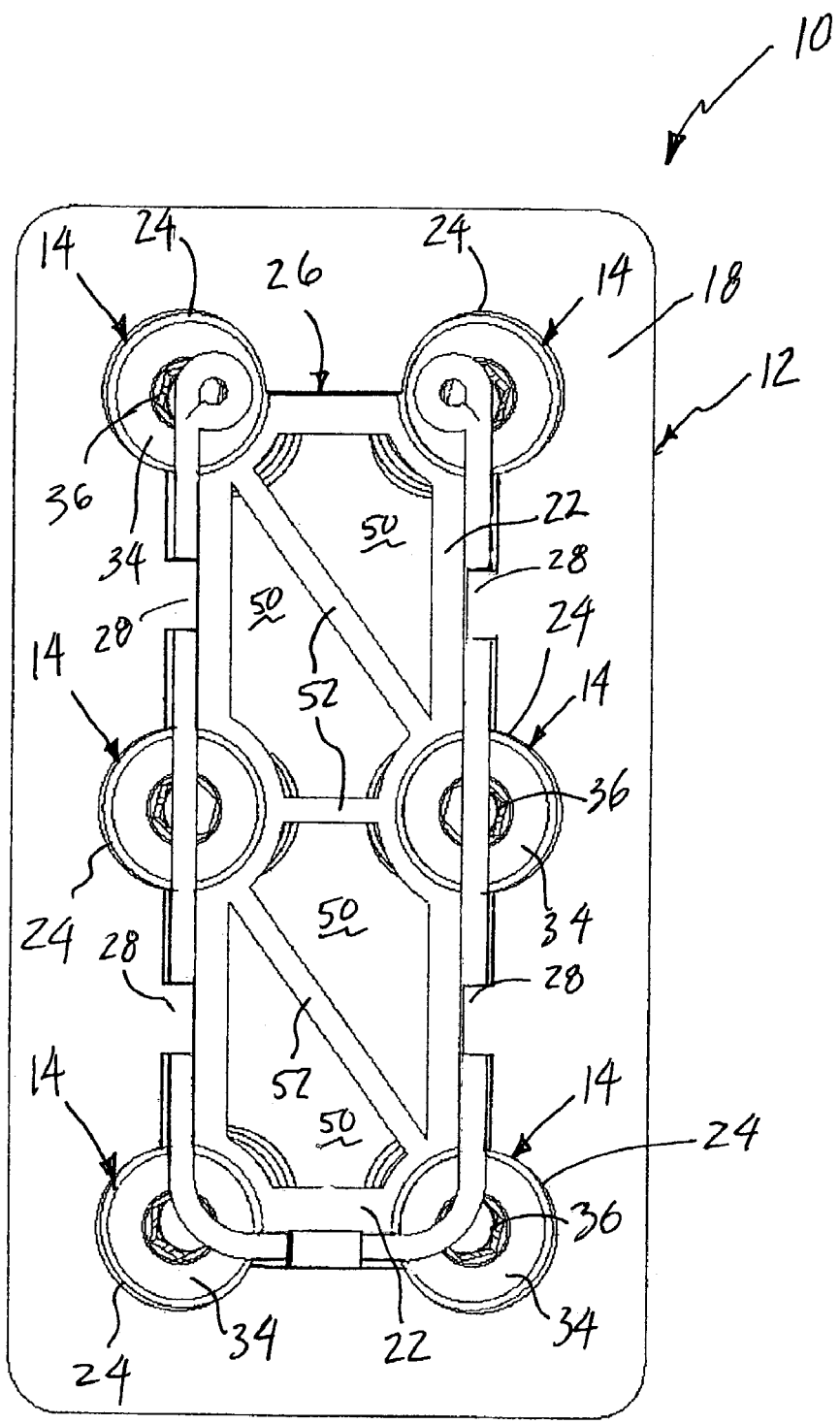
FIG. 8 is a top view of a surgical fixation system according to another aspect of the present invention.
Figure 9:
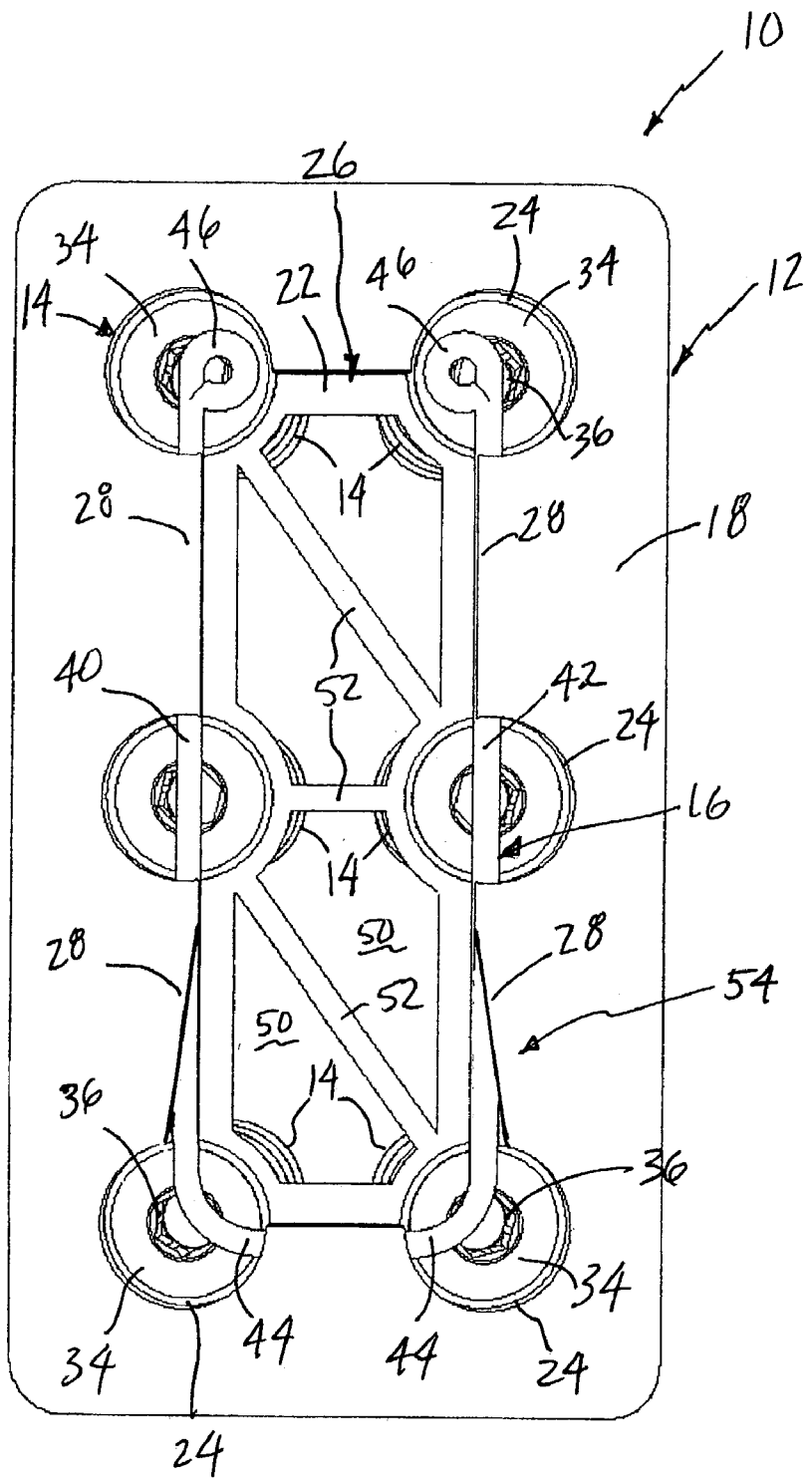
FIG. 9 is a top view of a surgical fixation system according to yet another aspect of the present invention.

The tab members 28 may also be dimensioned in any number of suitable fashions without departing from the scope of the present invention. For example, with reference to FIG. 8, the tab members 28 may extend a portion of the distance between adjacent fastener-receiving apertures 24 (as opposed to extending the entire distance as in the embodiment shown in FIGS. 1–7). As shown in FIG. 9, the individual shapes of the various tab members 28 may also be different, such as (by way of example only) providing one or more of the tab members 28 angled medially. In this fashion, the retainer-receiving aperture 26 will be defined to include a flared region 54 towards one end of the plate 12. The flared region 54 is suitable to accommodate the medial deformation of at least one of the first and second regions 40, 42 of the retainer 16 during introduction into the retainer-receiving aperture 26.

Figure 10:
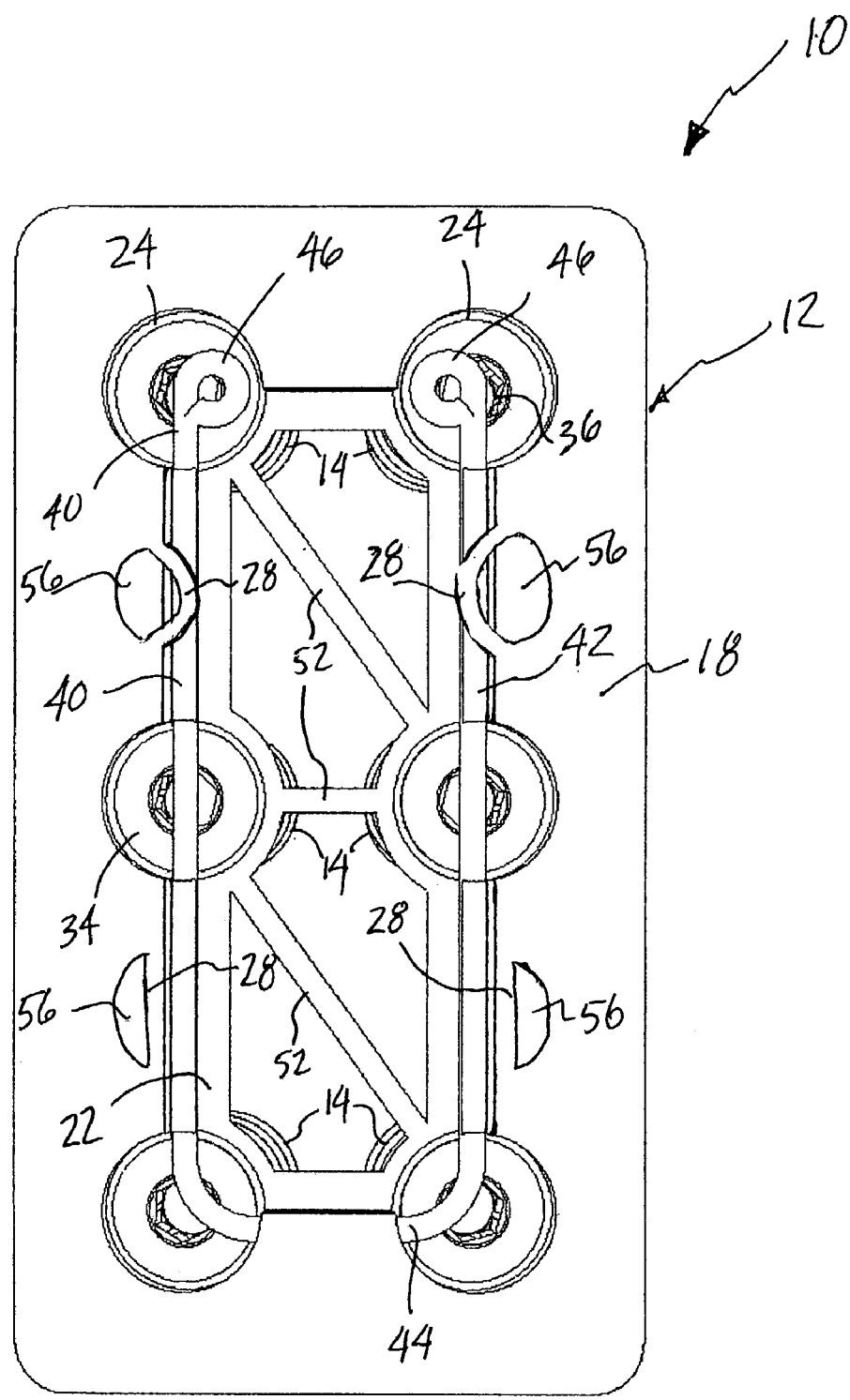
FIG. 10 is a top view of a surgical fixation system according to a still further aspect of the present invention.

FIG. 10 illustrates yet another manner of providing the tab members 28 according to a broad aspect of the present invention, wherein the tab members 28 are deformable in a generally medial direction to extend over at least a portion of the retainer 16. In one embodiment, this is accomplished by providing tab-deployment apertures 56 (extending part or the entire distance between the upper surface 18 and the lower surface 20) immediately lateral to the tab members 28. The tab members 28 may thus be selectively deformed to move from a first—undeployed—position (shown in the two-deployment apertures 56 closest to the third region 44 of the retainer 16) to a second—deployed—position (shown in the two tab-deployment apertures 56 closest to the loops 46 of the retainer 16). This may be accomplished in any number of suitable fashions, including but not limited to placing an instrument (such as a flat screwdriver) into the tab-deployment aperture 56 of an undeployed tab member 28 and actuating the instrument (such as via rotation in the case of a screwdriver) to thereby force the tab member 28 into position above at least a portion of the retainer 16.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as described herein.

What is claimed is:

1. A surgical fixation system, comprising:
   a plate having at least one fastener-receiving aperture and at least one retainer-receiving aperture, said fastener-receiving aperture extending between an upper surface and a lower surface of said plate, and said retainer-receiving aperture having a periphery defined by a plurality of tab members extending from said upper surface wherein at least a portion of said tab members are deformable from a first position to a second position, said first position permitting the introduction of said retainer into said retainer-receiving aperture, and said second position preventing the removal of said retainer from said retainer-receiving aperture;
   at least one fastener having an anchor region and a head region; said anchor region dimensioned to be passed through said fastener-receiving aperture for introduction into a surgical target site, and said head region dimensioned to be received at least partially within said fastener-receiving aperture; and
   at least one retainer dimensioned to be introduced into said retainer-receiving aperture to overlap at least a portion of said head region of said fastener and thereby prevent said fastener from backing out of said fastener-receiving aperture.

2. The surgical fixation system of claim 1 and further, wherein said retainer is hingedly coupled to said plate.

3. The surgical fixation system of claim 1 and further, wherein said plate includes a plurality of said fastener-receiving apertures, and wherein said tab members extend between at least two of said plurality of fastener-receiving apertures.

4. The surgical fixation system of claim 1 and further, wherein said plate includes a plurality of said fastener-receiving apertures, and wherein said tab members extend a portion of the distance between at least two of said fastener-receiving apertures.

5. The surgical fixation system of claim 1 and further, wherein said tab members extend generally medially from said upper surface of said plate to define said first position, and wherein at portion of said tab members may be bent towards said lower surface to define said second position.

6. The surgical fixation system of claim 1 and further, wherein said tab members extend generally parallel from said upper surface to define said first position, and wherein at least a portion of said tab members may be bent medially from said upper surface to define said second position.

7. The surgical fixation system of claim 1 and further, wherein said fastener-receiving aperture may include at least one of a circular aperture and an elongated slot-type aperture.

8. The surgical fixation system of claim 1 and further, wherein said retainer includes a first region, a second region disposed generally parallel to said first region, and a third region extending generally perpendicularly between said first and second regions, at least one of said first and second regions being temporarily medially deformable such that said retainer may be introduced into said retainer-receiving aperture and thereafter moved laterally to position said retainer at least partially under said tab members.

9. The surgical fixation system of claim 8 and further, wherein said retainer comprises a generally U-shaped member.

10. The surgical fixation system of claim 9 and further, wherein said retainer includes an instrument purchase region dimensioned to engage with an insertion instrument.

11. The surgical fixation system of claim 10 and further, wherein said instrument purchase region comprises a loop dimensioned to receive a portion of said insertion instrument therein.

12. The surgical fixation system of claim 9 and further, wherein at least one of said tab members is angled medially such that said retainer-receiving aperture includes flared region towards one end of said plate suitable to accommodate said medial deformation of at least one of said first and second regions of said retainer during introduction into said retainer-receiving aperture.

13. The surgical fixation system of claim 1 and further, wherein said plate includes at least one viewing aperture to permit viewing through said plate.

14. The surgical fixation system of claim 13 and further, wherein said at least one viewing aperture is defined by at least one brace member extending between locations on said lower surface of said plate.

15. The surgical fixation system of claim 14 and further, wherein said at least one brace member extends from a location on said lower surface of said plate generally adjacent to at least one of said fastener-receiving apertures.

16. A method of surgical fixation, comprising the steps of:
(a) positioning a plate over an intended surgical target site, said plate having at least one fastener-receiving aperture and at least one retainer-receiving aperture, said fastener-receiving aperture extending between an upper surface and a lower surface of said plate, and said retainer-receiving aperture having a periphery defined by a plurality of tab members extending from said upper surface wherein at least a portion of said tab members are deformable from a first position to a second position, said first position permitting the introduction of said retainer into said retainer-receiving aperture, and said second position preventing the removal of said retainer from said retainer-receiving aperture;
(b) introducing a fastener into said fastener-receiving aperture such that an anchor region of said fastener is introduced into said surgical target site and a head region of said fastener is receiving at least partially within said fastener-receiving aperture; and
(c) introducing a retainer into said retainer-receiving aperture to overlap at least a portion of said head region of said fastener and thereby prevent said fastener from backing out of said fastener-receiving aperture.

17. The method of surgical fixation of claim 16 and further, wherein said retainer is hingedly coupled to said plate.

18. The method of surgical fixation of claim 16 and further, wherein said plate includes a plurality of said fastener-receiving apertures, and wherein said tab members extend between at least two of said plurality of fastener-receiving apertures.

19. The method of surgical fixation of claim 16 and further, wherein said plate includes a plurality of said fastener-receiving apertures, and wherein said tab members extend a portion of the distance between at least two of said fastener-receiving apertures.

20. The method of surgical fixation of claim 16 and further, wherein said tab members extend generally medially from said upper surface of said plate to define said first position, and wherein at portion of said tab members may be bent towards said lower surface to define said second position.

21. The method of surgical fixation of claim 16 and further, wherein said tab members extend generally parallel from said upper surface to define said first position, and wherein at least a portion of said tab members may be bent medially from said upper surface to define said second position.

22. A method of surgical fixation of claim 16 and further, wherein said fastener-receiving aperture may include at least one of a circular aperture and an elongated slot-type aperture.

23. A method of surgical fixation of claim 16 and further, wherein said retainer includes a first region, a second region disposed generally parallel to said first region, and a third region extending generally perpendicularly between said first and second regions, at least one of said first and second regions being temporarily medially deformable such that said retainer may be introduced into said retainer-receiving aperture and thereafter moved laterally to position said retainer at least partially under said tab members.

24. The method of surgical fixation of claim 23 and further, wherein said retainer comprises a generally U-shaped member.

25. The method of surgical fixation of claim 24 and further, wherein said retainer includes an instrument purchase region dimensioned to engage with an insertion instrument.

26. The method of surgical fixation of claim 25 and further, wherein said instrument purchase region comprises a loop dimensioned to receive a portion of said insertion instrument therein.

27. The method of surgical fixation of claim 24 and further, wherein at least one of said tab members is angled medially such that said retainer-receiving aperture includes flared region towards one end of said plate suitable to accommodate said medial deformation of at least one of said first and second regions of said retainer during introduction into said retainer-receiving aperture.

28. The method of surgical fixation of claim 16 and further, wherein said plate includes at least one viewing aperture to permit viewing through said plate.

29. The method of surgical fixation of claim 28 and further, wherein said at least one viewing aperture is defined by at least one brace member extending between locations on said lower surface of said plate.

30. The method of surgical fixation of claim 29 and further, wherein said at least one brace member extends from a location on said lower surface of said plate generally adjacent to at least one of said fastener-receiving apertures.

* * * * *